United States Patent [19]

Zweig et al.

[11] 4,304,949

[45] Dec. 8, 1981

[54] SYNTHESIS OF ORTHO-METHYLDIPHENYLMETHANE

[75] Inventors: Arnold Zweig, Westport; Robert G. Fischer, Fairfield, both of Conn.

[73] Assignee: American Cyanamid Company, Stamford, Conn.

[21] Appl. No.: 172,358

[22] Filed: Jul. 25, 1980

[51] Int. Cl.³ .......................... C07C 2/02; C07C 6/12; C07C 13/28
[52] U.S. Cl. .................................... 585/422
[58] Field of Search ........................................ 585/422

[56] References Cited

U.S. PATENT DOCUMENTS

| 2,557,505 | 6/1951 | Ipatieff et al. | 585/422 |
| 2,671,815 | 3/1954 | Pines et al. | 585/422 |
| 2,742,516 | 4/1956 | Schneider | 585/422 |
| 2,759,984 | 8/1956 | Schlatter | 585/422 |
| 2,954,412 | 9/1960 | Wulf et al. | 585/422 |
| 3,833,677 | 9/1974 | Grard | 585/422 |
| 4,117,019 | 9/1978 | Eilingsfeld et al. | 585/422 |

FOREIGN PATENT DOCUMENTS 824878 12/1959 United Kingdom ................ 585/422

*Primary Examiner*—Paul F. Shaver
*Attorney, Agent, or Firm*—Bruce F. Jacobs

[57] ABSTRACT

A process for the preparation of ortho-methyldiphenylmethane, a compound useful as an intermediate in the synthesis of anthraquinone, using liquid hydrogen fluoride to catalyze the alkylation of benzene with $\alpha$-chloro-o-xylene at temperatures from about $-10°$ C. to $10°$ C.

8 Claims, No Drawings

SYNTHESIS OF ORTHO-METHYLDIPHENYLMETHANE

The present invention relates to a method of preparing ortho-methyldiphenylmethane, a compound of the formula:

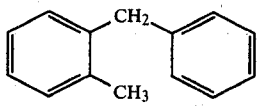

and a direct precursor to anthraquinone. Anthraquinone, in turn, finds widespread commercial use in the manufacture of dyes and dye intermediates and also serves to increase the yield of usable cellulose obtainable from wood in the pulping-delignification step of paper manufacturing. More particularly, this invention relates to the production of ortho-methyldiphenylmethane, in the substantial absence of isomers thereof, by the reaction of benzene and α-chloro-o-xylene at temperatures from about $-10°$ C. to $10°$ C. in the presence of liquid hydrogen fluoride as the catalyst.

The use of hydrogen fluoride as the catalyst in some benzene alkylations has been known. It has been used, presumably in the vapor phase, to catalyze the reaction of benzene with benzyl chloride at $100°$ C. for 15 hours to yield diphenylmethane (Simmons and Archer, 61 J. Am. Chem. Soc'y at 1521 (1939)), but the yield in that reaction was only 56 percent. U.S. Pat. No. 3,109,868 discloses an aromatic compound alkylation with a para-substituted benzyl halide in the presence of a hydrogen fluoride catalyst, but no conditions for the reaction are specified.

Neither of the above references appreciates the effect of temperature in minimizing isomerization in substituted benzene alkylations generally, or in the present ortho-substituted benzene alkylation specifically. In addition, no use of hydrogen fluoride as a catalyst for the alkylation of benzene with α-chloro-o-xylene to yield the ortho isomer of methyldiphenylmethane has been found.

Currently, ortho-methyldiphenylmethane (o-MDPM) is produced by the alkylation of benzene with α-chloro-o-xylene (α-ClOX) in the presence of one of a variety of catalysts, among them being aqueous sulfuric acid and metal halides. Although 80% by weight sulfuric acid appears to be the most efficient catalyst utilized in the art, it is time consuming (4 to 6 hour reaction time) and requires substantial energy input ($80°$ to $85°$ C. reaction temperature). Also, sulfonation of the benzene is a side reaction of the alkylation which leads to unwanted foaming and difficulty in layer separation.

It is an object of this invention to provide a process for synthesizing o-MDPM which substantially avoids production of isomers thereof. It is a further object of this invention to provide a process for producing o-MDPM which ameliorates the foaming and layer separation problems encountered in the sulfuric acid catalyzed alkylation of benzene with α-ClOX. It is yet another object of the invention to provide a process for producing o-MDPM which saves time and conserves energy by operating more rapidly and at reduced temperatures in comparison to the sulfuric acid catalyzed process. Other objects and advantages of the invention will become apparent from a consideration of the ensuing description.

It has been discovered that o-MDPM can be prepared in a short time and in good yield and high purity by subjecting a benzene and α-ClOX mixture to the action of liquid hydrogen fluoride within a narrow temperate range, i.e., from about $-10°$ C. to $10°$ C. Benzene and hydrogen fluoride are readily commercially available, and α-chloro-o-xylene may be produced by any one of a number of methods well known in the art, the particular process employed in its preparation not constituting a feature of this invention.

Generally, the present reaction will take less than two hours and, upon completion, the product and catalyst are easily separated, thereby permitting catalyst recovery for re-use without large energy expenditure.

The temperature at which the reaction is conducted is the most important factor in eliminating the isomerization of the product. Normally, the reaction is run at temperatures from about $-10°$ C. to $10°$ C., with from about $-5°$ C. to $5°$ C. preferred and $0°$ C. most preferred. Running the reaction at ambient temperatures (i.e., $20°$ C. to $30°$ C.) or higher results in undesired isomerization to products which cannot function as intermediates in the synthesis of anthraquinone. While the reaction might be carried out at temperatures lower than $-10°$ C., there is believed to be no advantage in doing so.

The amount of liquid hydrogen fluoride used has been found to be not critical to the rate of the reaction. However, the presence of a layer of liquid hydrogen fluoride was found to be important in causing the reaction to proceed to completion within two hours. Subject to the desirability of having a liquid layer of HF present, generally from about 10 to 125% by weight of the mixture of benzene and αα-ClOX is used, and preferably from about 75 to 100%.

Molar ratios of benzene to α-ClOX in the reaction may range from about 5 to 10:1, with from about 8 to 10:1 preferable. Any excess benzene may be recovered from the reaction product and reused.

In order to facilitate a better understanding of the invention, the following examples are presented primarily for the purpose of illustrating more specific details thereof. The invention is not deemed limited thereby, except as defined in the appended claims. All parts and percents are by weight unless otherwise specified.

EXAMPLE 1

A reaction apparatus was charged with about 30 g. of anhydrous hydrogen fluoride under nitrogen at $-78°$ C. The hydrogen fluoride was warmed to $0°$ C. and a mixture of benzene (29.63 g., 0.38 moles) and α-chloro-o-xylene (5.55 g., 0.0395 moles) was injected into the liquid hydrogen fluoride over a two minute period. The mixture was stirred, an emulsion formed, and hydrogen chloride was liberated. After about 15 minutes, two liquid layers formed.

Stirring of the mixture was continued for 1.75 hours at $0°$ C., whereupon the reaction was quenched in a mixture of chloroform and ice.

The chloroform layer, containing the reaction product, was easily separated, washed with water, dried over sodium sulfate and concentrated to give 8.30 g. of product.

Analysis of the product showed it contained 80 percent methyldiphenylmethane (the equivalent of a 92 percent yield), and only the ortho isomer of the compound was present.

EXAMPLE 2

The procedure of Example 1 was repeated three more times, with amounts of reactants and catalyst, and the reaction time, varied as set forth in Table I below.

TABLE I

| g. α-ClOX | g. Benzene | g. HF (Approx.) | T(°C.) | Time (Hrs.) | Actual % Yield MDPM | Isomer Purity |
|---|---|---|---|---|---|---|
| 5.6 | 14.4 | 25 | 0 | 1.25 | 91% | at least 95% o-MDPM |
| 5.6 | 29.9 | 4 | 0 | 1.75 | 84% | at least 95% o-MDPM |
| 5.34 | 28.5 | 30 | 0 | 1.75 | 90.4% | at least 95% o-MDPM |

Table I illustrates that the molar ratio of benzene to α-ClOX may range from about 5 to 10:1, with the yield and purity of o-MDPM remaining good. Also, significantly lowering the amount of hydrogen fluoride used did not materially adversely affect the yield of o-MDPM (Run No. 2).

EXAMPLE 3

The procedure of Example 1 is repeated, except that the reaction takes place at −10°, −5°, and 10° C.

Substantially equivalent results are obtained.

EXAMPLE 4

This example evidences the importance of the temperature at which the hydrogen fluoride catalyzed alkylation occurs.

29.9 g. (0.4 moles) of benzene was frozen with a dry ice-acetone mixture, after having been flushed with nitrogen. About 40 g. of liquid hydrogen fluoride was added to the benzene and the mixture was allowed to warm until most of the benzene had melted, thereby forming two layers. Thereupon, 6.17 g. (0.044 moles) of α-chloro-o-xylene was injected into the mixture over a 15 minute period. Emulsification of the layers ensued, and HCl was liberated. The mixture was then stirred for four hours at room temperature (19.5° C.).

The reaction mixture was then treated as in Example 1, and 8.93 g. of product was recovered. Analysis of the product disclosed that, in addition to the desired ortho isomer of methyldiphenylmethane, 16 percent of the product was composed of other isomers of methyldiphenylmethane. Those isomers cannot function as intermediates in the synthesis of anthraquinone.

What is claimed is:

1. A process for preparing ortho-methyldiphenylmethane which comprises reacting a mixture of benzene and α-chloro-o-xylene in the presence of a catalytically effective amount of liquid hydrogen fluoride at a temperature from about −10° C. to 10° C.

2. The process of claim 1 wherein the hydrogen fluoride forms a continuous layer.

3. The process of claim 1 wherein the hydrogen fluoride is present in an amount from about 10% to 125% by weight of the mixture of benzene and α-chloro-o-xylene.

4. The process of claim 1 wherein the hydrogen fluoride is present in an amount from about 25% to 100% by weight of the mixture of benzene and α-chloro-o-xylene.

5. The process of claim 1 wherein the molar ratio of benzene to α-chloro-o-xylene is from about 5 to 10:1.

6. The process of claim 1 wherein the molar ratio of benzene to α-chloro-o-xylene is from about 8 to 10:1.

7. The process of claim 1 wherein the reaction is conducted at a temperature of from about −5° C. to 5° C.

8. The process of claim 1 wherein the reaction is conducted at 0° C.

* * * * *